United States Patent
Umakoshi et al.

(10) Patent No.: US 7,893,611 B2
(45) Date of Patent: Feb. 22, 2011

(54) METAL COMPLEX, LIGHT-EMITTING DEVICE AND DISPLAY

(75) Inventors: Keisuke Umakoshi, Nagasaki (JP); Seiji Akatsu, Nagasaki (JP); Masayoshi Onishi, Nagasaki (JP); Shoji Ishizaka, Sapporo (JP); Noboru Kitamura, Sapporo (JP)

(73) Assignee: Nagasaki University, Nagasaki-shi, Nagasaki (JP)

( * ) Notice: Subject to any disclaimer, the term of this patent is extended or adjusted under 35 U.S.C. 154(b) by 0 days.

(21) Appl. No.: 12/444,826

(22) PCT Filed: Nov. 1, 2007

(86) PCT No.: PCT/JP2007/071348

§ 371 (c)(1),
(2), (4) Date: Apr. 8, 2009

(87) PCT Pub. No.: WO2008/053976

PCT Pub. Date: May 8, 2008

(65) Prior Publication Data

US 2010/0010231 A1    Jan. 14, 2010

(30) Foreign Application Priority Data

Nov. 1, 2006 (JP) ............... 2006-297938
Mar. 6, 2007 (JP) ............... 2007-056126
Mar. 22, 2007 (JP) ............... 2007-075105

(51) Int. Cl.
*C07F 19/00* (2006.01)
*H01L 31/00* (2006.01)

(52) U.S. Cl. ............ 313/504; 257/13; 257/40; 313/483; 548/101; 548/365.1; 548/373.1

(58) Field of Classification Search ............. 257/13, 257/40; 313/483, 504; 548/101, 365.1, 373.1
See application file for complete search history.

(56) References Cited

FOREIGN PATENT DOCUMENTS

WO    WO 2006/101276 A1    9/2006

OTHER PUBLICATIONS

U.S. Appl. No. 11/909,686, filed Mar. 13, 2009, Umakoshi, et al.

International Search Report issued in PCT/JP2007/071348 (Published as WO 2008/053976 A1) Nov. 29, 2007, and English-language translation.
International Preliminary Report on Patentability and Written Opinion issued in PCT/JP2007/071348 (Published as WO 2008/053976 A1) May 5, 2009, and English-language translations.
Baldo, M.A., et al., "Very high-efficiency green organic light-emitting devices based on electrophosphorescence," *Applied Physics Letters*, Jul. 5, 1999, pp. 4-6, vol. 75, No. 1, American Institute of Physics, USA.
Lai, S.W., et al., "Luminescent Cyclometalated Diimine Platinum (II) Complexes: Photophysical Studies and Applications," *Top. Curr. Chem.*, 2004, pp. 27-63, vol. 241, Springer-Verlag, Berlin, DE.
Dias, H. V. Rasika, et al., "Brightly Phosphorescent Trinuclear Copper(I) Complexes of Pyrazolates: Substituent Effects on the Supramolecular Structure and Photophysics," *J. Am. Chem. Soc.*, 2005, pp. 7489-7501, vol. 127, American Chemical Society, USA.
Ardizzoia, G. Attilio, et al., "Polynuclear Pyrazolato complexes. Synthesis, chemical reactivity and crystal structures of [{Pd(dmpz)$_2$(Hdmpz)$_2$}$_2$] and [{PdAg$_2$(dmpz)$_4$}$_2$] (Hdmpz=3,5-dimethylpyrazole)," *J. Chem. Soc., Dalton Trans.*, 1996, pp. 1351-1357, Royal Society of Chemistry, UK.
Umakoshi, Keisuke, et al., "Pyrazolato-Bridged Polynuclear Palladium and Platinum Complexes. Synthesis, Structure, and Reactivity", *Inorganic Chemistry*, 2003, pp. 3907-3916, vol. 42, No. 12, American Chemical Society, USA.

*Primary Examiner*—Golam M. M. Shameem
*Assistant Examiner*—Samantha L Shterengarts
(74) *Attorney, Agent, or Firm*—Buchanan Ingersoll & Rooney PC (57) ABSTRACT

There is provided a novel luminescent metal complex. A metal complex having a composition of $[(Pt^{II})_2(M^I)_2(X)_2(L)_4(LH)_2]$, where $M^I$ denotes $Ag^I$, $Au^I$ or $Cu^I$, X denotes Cl, Br or I, L denotes a structure represented by the formula (1), and LH denotes a structure represented by the formula (2).

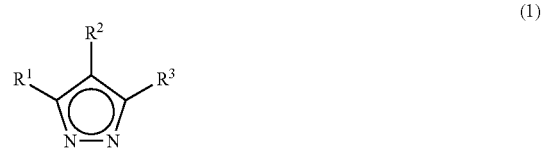

(1)

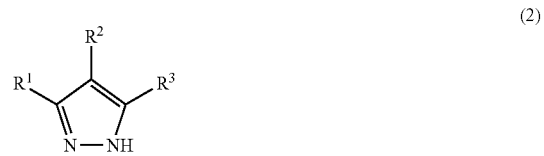

(2)

10 Claims, 5 Drawing Sheets

METAL COMPLEX, LIGHT-EMITTING DEVICE AND DISPLAY

TECHNICAL FIELD

The present invention relates to a metal complex. The present invention also relates to a light-emitting device including a light-emitting layer including the metal complex. The present invention further relates to a display including the light-emitting device.

BACKGROUND ART

Recently, organic EL devices have attracted attention as light-emitting displays alternative to liquid crystal displays. Organic EL devices of the related art utilize emission (fluorescence) from a singlet excited state. In this case, a local maximum emission efficiency is 25% based on a principle of an organic EL phenomenon, and therefore emission is extremely insufficient.

Phosphorescence generated from a triplet excited state has attracted most attention recently as a method of increasing emission efficiency (see Non-Patent Document 1, for example).

In this case, the emission efficiency may be 100% in theory.

Many $Pt^{II}$, complexes having diimine or terpyridine and their derivatives exhibit emission which are assigned to MLCT (abbreviation of metal-to-ligand charge transfer; charge transfer from a metal ion to a ligand) or MMLCT (abbreviation of metal-metal-to-ligand charge transfer; charge transfer from a $d\sigma^*$ orbital formed by metal-metal interaction to a ligand), and photochemical properties of these compounds have attracted much interest (See Non-Patent Document 2, for example).

Polynuclear $Cu^I$ and $Au^I$ complexes of pyrazolate and its derivatives are also known to exhibit emission (see Non-Patent Document 3, for example).

Accordingly, when a molecule is synthesized with $Pt^{II}$ ions and $Cu^I$ ions, $Ag^I$ ions or $Au^I$ ions and these metal ions are bridged by pyrazolate or its derivatives, it is promising to produce a new molecule having emission properties by a synergetic effect of different metal ions.

In development of a novel metal complex based on this idea, a mixed metal complex $[Pd_2Ag_4(\mu\text{-dmpz})_8]$ having two $Pd^{II}$ ions and four $Ag^I$ ions bridged by 3,5-dimethylpyrazolate ligands (see Non-Patent Document 4) is known as an analogous compound; however, emission properties of this compound have never been reported.

The present inventors also have already synthesized a mixed metal complex $[Pt_2Ag_4(\mu\text{-pz})_8]$ having $Pt^{II}$ ions and $Ag^I$ ions bridged by pyrazolate ligands without substituent groups (see Non-Patent Document 5); however, this compound does not show emission.

Furthermore, in development of displays for commercialization, there is an increasing demand for a novel metal complex used as a dopant having improved thermal stability, volatility, film-forming properties during deposition, solubility in various solvents, emission intensity, color purity, and stability when applying a potential.

[Non-Patent Document 1] M. A. Baldo, S. Lamansky, P. E. Burrows, M. E. Thompson, S. R. Forrest, Appl. Phys. Lett., 1999, 75, 4-6.

[Non-Patent Document 2] S.-W. Lai, C.-M. Che, Topics in Current Chemistry, 2004, 241 (Transition Metal and Rare Earth Compounds III), 27-63.

[Non-Patent Document 3] H. V. R. Dias, H. V. K. Diyabalanage, M. G. Eldabaja, O. Elbjeirami, M. A. Rawashdeh-Omary, M. A. Omary, J. Am. Chem. Soc., 2005, 127, 7489-7501.

[Non-Patent Document 4] G. A. Ardizzoia, G. La Monica, S. Cenini, M. Moret, N. Masciocchi, J. Chem. Soc., Dalton Trans. 1996, 1351-1357.

[Non-Patent Document 5] K. Umakoshi, Y. Yamauchi, K. Nakamiya, T. Kojima, M. Yamasaki, H. Kawano, M. Onishi, Inorg. Chem. 2003, 42, 3907-3916.

DISCLOSURE OF THE INVENTION

The present invention has been attempted to solve such a problem. An object of the present invention is to provide a novel luminescent metal complex.

Another object of the present invention is to provide a novel light-emitting device including the metal complex in a light-emitting layer.

Still another object of the present invention is to provide a novel display including the light-emitting device as a component.

In order to solve the aforementioned problem and achieve the object of the present invention, a first metal complex of the present invention includes a composition of where $M^I$ denotes $Ag^I$, $Cu^I$ or $Au^I$, X denotes Cl, Br or I, L denotes each or a combination of any of structures represented by the formula (1), and LH denotes each or a combination of any of structures represented by the formula (2).

Although the five-membered ring moiety of the formula (2) is described differently from that of the formula (1), both formulas are substantially identical in structure. Here, LH denotes an uncharged pyrazole compound, and L denotes a monovalent anion in which a proton is dissociated from the pyrazole compound.

[Chemical formula 1]

(1)

[Chemical formula 2]

(2)

In the formulas, $R^1$, $R^2$ and $R^3$ independently denote a hydrogen atom, a chlorine atom, a bromine atom, an iodine atom, a hydroxyl group, a phenyl group, a trifluoromethylphenyl group, a pentafluorophenyl group, a naphthyl group, a methyl group, an ethyl group, an i-propyl group, a t-butyl group, a trifluoromethyl group, a hydroxymethyl group or a hydroxyethyl group.

More preferably, at least one of $R^1$, $R^2$ and $R^3$ in the formulas (1) and (2) is not a hydrogen atom.

A light-emitting device of the present invention includes a light-emitting layer including the first metal complex of the present invention.

A display of the present invention includes the light-emitting device.

A second metal complex of the present invention includes a composition of where X denotes Cl, Br or I, and L denotes each or a combination of any of structures represented by the formula (1):

[Chemical formula 1]

(1)

where $R^1$, $R^2$ and $R^3$ independently denote a hydrogen atom, a chlorine atom, a bromine atom, an iodine atom, a hydroxyl group, a phenyl group, a trifluoromethylphenyl group, a pentafluorophenyl group, a naphthyl group, a methyl group, an ethyl group, an i-propyl group, a t-butyl group, a trifluoromethyl group, a hydroxymethyl group or a hydroxyethyl group.

More preferably, at least one of $R^1$, $R^2$ and $R^3$ in the formula (1) is not a hydrogen atom.

A light-emitting device of the present invention includes a light-emitting layer including the second metal complex of the present invention.

A display of the present invention includes the light-emitting device.

The present invention has the following effect.

The metal complex of the present invention may provide a metal complex having excellent emission properties.

The light-emitting device of the present invention includes a light-emitting layer including the metal complex of the present invention, and thus may provide a light-emitting device having improved emission properties.

The light-emitting apparatus of the present invention includes the light-emitting device, and thus may display a high-quality image and realize a reliable light-emitting apparatus.

BEST MODE FOR CARRYING OUT THE INVENTION

A best mode for carrying out the present invention will be described below.

Metal complexes of the present invention will be described.

A first metal complex of the present invention includes a composition represented by the following formula:

where $M^I$ denotes $Ag^I$, $Cu^I$ or $Au^I$, X denotes Cl, Br or I, L denotes each or a combination of any of structures represented by the formula (1), and LH denotes each or a combination of any of structures represented by the formula (2).

In the formulas, $R^1$, $R^2$ and $R^3$ independently denote a hydrogen atom, a chlorine atom, a bromine atom, an iodine atom, a hydroxyl group, a phenyl group, a trifluoromethylphenyl group, a pentafluorophenyl group, a naphthyl group, a methyl group, an ethyl group, an i-propyl group, a t-butyl group, a trifluoromethyl group, a hydroxymethyl group or a hydroxyethyl group.

More preferably, at least one of $R^1$, $R^2$ and $R^3$ in the formulas (1) and (2) is not a hydrogen atom, that is, at least one of $R^1$, $R^2$ and $R^3$ is a substituent group.

A second metal complex of the present invention includes a composition of where X denotes Cl, Br or I, and L denotes each or a combination of any of structures represented by the formula (1).

In the formulas, $R^1$, $R^2$ and $R^3$ independently denote a hydrogen atom, a chlorine atom, a bromine atom, an iodine atom, a hydroxyl group, a phenyl group, a trifluoromethylphenyl group, a pentafluorophenyl group, a naphthyl group, a methyl group, an ethyl group, an i-propyl group, a t-butyl group, a trifluoromethyl group, a hydroxymethyl group or a hydroxyethyl group.

More preferably, at least one of $R^1$, $R^2$ and $R^3$ in the formula (1) is not a hydrogen atom, that is, at least one of $R^1$, $R^2$ and $R^3$ is a substituent group.

In the next part, the synthesis of the metal complexes of the present invention will be described.

In the following, dppzH denotes 3,5-diphenylpyrazole, and dppz denotes a monovalent anion in which a proton is dissociated from 3,5-diphenylpyrazole.

First, the synthetic method of [PtCl(dppz)(dppzH)$_2$] will be described as an example of a precursor complex for the metal complexes of the present invention.

This precursor complex [PtCl(dppz)(dppzh)$_2$] may be synthesized by the following procedure, for example.

The reaction of [PtCl$_2$(C$_2$H$_5$CN)$_2$] with dppzH, and the successive treatment of resulting white yellow precipitate with KOH gives [PtCl(dppz)(dppzH)$_2$]. [PtBr(dppz)(dppzH)$_2$] and [PtI(dppz)(dppzH)$_2$] may be synthesized similarly.

The synthetic method of [PtX(dppz)(dppzH)$_2$] (X=Cl⁻, Br⁻ or I⁻) is not limited to the aforementioned method. There is also the following other preparative method.

[PtX$_2$(C$_2$H$_5$CN)$_2$] is suspended in water, methanol or ethanol. An excess amount of dppzH is added to the suspension, and the mixture is refluxed for one hour. The solution is allowed to cool and then concentrated under reduced pressure, and acetone or diethyl ether is added to the residue to form a precipitate. The formed precipitate is treated with a base such as NaOH or KOH, and the resulting solid is washed with methanol and water and then dried in vacuo.

Next, the synthetic method of [Pt$_2$Ag$_2$Cl$_2$(μ-dppz)$_4$(μ-dppzH)$_2$] will be described as an example of the first metal complex of the present invention. This metal complex is the first metal complex of the present invention, where M is Ag and X is Cl.

The reaction of the precursor complex [PtCl(dppz)(dppzH)$_2$], which is synthesized by the above described procedure, with AgBF$_4$ gives [Pt$_2$Ag$_2$Cl$_2$(μ-dppz)$_4$(μ-dppzH)$_2$].

The reaction of [PtCl(dppz)(dppzH)$_2$] with AgBF$_4$ in the presence of triethylamine gives a metal complex [Pt$_2$Ag$_4$(μ-Cl)$_2$(μ-dppz)$_6$].

The metal complex [Pt$_2$Ag$_2$Cl$_2$(μ-dppz)$_4$(μ-dppzH)$_2$] is a compound in which some dppzH ligands are not deprotonated and coordinate in an uncharged state.

Protons of dppzH ligands of the metal complex are replaced by silver ions to form Ag—Cl bonds, thus forming the metal complex [Pt$_2$Ag$_4$(μ-Cl)$_2$(μ-dppz)$_6$].

This is also proved from the fact that the addition of a silver ion (such as AgBF$_4$) and a base (such as triethylamine) to the metal complex [Pt$_2$Ag$_2$Cl$_2$(μ-dppz)$_4$(μ-dppzH)$_2$] affords the metal complex [Pt$_2$Ag$_4$(μ-Cl)$_2$(μ-dppz)$_6$].

Next, the synthetic method of [Pt$_2$Cu$_2$Cl$_2$(μ-dppz)$_4$(μ-dppzH)$_2$] will be described as an example of the first metal complex of the present invention. This metal complex is the first metal complex of the present invention, where M is Cu and X is Cl.

The reaction of the precursor complex [PtCl(dppz)(dppzH)$_2$] with [Cu(CH$_3$CN)$_4$]BF$_4$ gives [Pt$_2$Cu$_2$Cl$_2$(μ-dppz)$_4$(μ-dppzH)$_2$].

Next, the synthetic method of [Pt$_2$Ag$_2$Cu$_2$(μ-Cl)$_2$(μ-dppz)$_6$] will be described as an example of the second metal complex of the present invention. This metal complex is the second metal complex of the present invention, where X is Cl.

The reaction of the metal complex [PtCl(dppz)(dppzH)$_2$] synthesized as described above with AgBF$_4$ gives a precursor complex [Pt$_2$Ag$_2$Cl$_2$(μ-dppz)$_4$(μ-dppzH)$_2$] (an example of the first metal complex of the present invention).

The reaction of the precursor complex [Pt$_2$Ag$_2$Cl$_2$(μ-dppz)$_4$(μ-dppzH)$_2$] with [Cu(CH$_3$CN)$_4$]BF$_4$ gives [Pt$_2$Ag$_2$Cu$_2$(μ-Cl)$_2$(μ-dppz)$_6$].

The synthetic method of [Pt$_2$Ag$_2$Cu$_2$(μ-Cl)$_2$(μ-dppz)$_6$] is not limited to the aforementioned method.

In the next part, the use of the metal complexes of the present invention will be described. The metal complexes can be used as luminescent agents contained in a light-emitting layer of a light-emitting device such as an organic EL device.

However, the metal complexes may not be only used as luminescent agents. The metal complexes can also be used as sensors for organic molecules or gas molecules, antitumor agents, or paints that are usually colorless and transparent but emit light only upon exposure to UV radiation, for example.

Next, a light-emitting device including such metal complexes in a light-emitting layer will be described.

Figure 1:
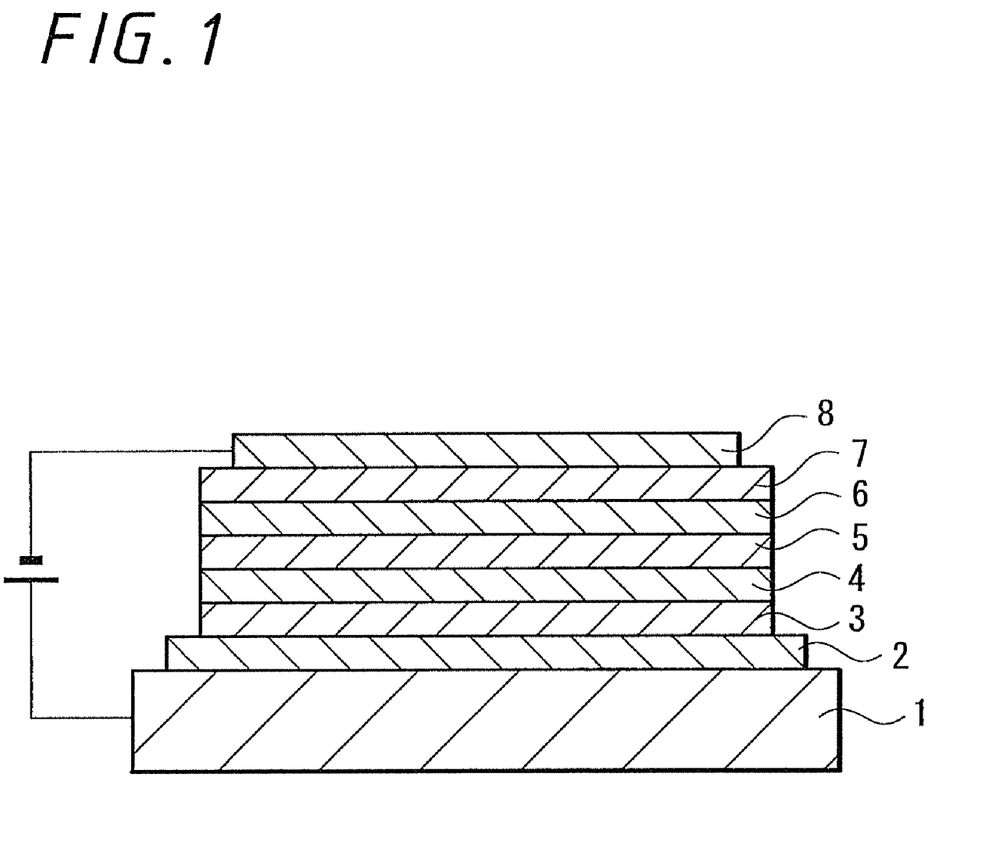
FIG. 1 is a cross-sectional view showing an example of a light-emitting device of the present invention.

FIG. 1 is a cross-sectional view showing an example of a light-emitting device of the present invention.

A substrate 1 is formed of a transparent material such as glass. An anode 2 is formed on the substrate 1. A hole injection layer 3, a hole transport layer 4, a light-emitting layer 5, an electron transport layer 6 and an electron injection layer 7 are formed on the anode 2. A cathode 8 is formed on the electron injection layer 7.

The light-emitting device of the present invention is not limited to the aforementioned five-layer light-emitting device.

Alternatively, the light-emitting device may be a four-layer light-emitting device in which the electron transport layer is omitted from the five-layer light-emitting device. The light-emitting device may also be a three-layer light-emitting device in which the hole injection layer and the electron injection layer are omitted from the five-layer light-emitting device. The light-emitting device may also be a two-layer light-emitting device having one layer used as both a light-emitting layer and an electron transport layer of the three-layer light-emitting device. The light-emitting device may also be a single-layer light-emitting device having only a light-emitting layer formed between an anode and a cathode.

The light-emitting device in which the aforementioned metal complexes may be advantageously used is essentially a light-emitting device including metal complexes having light-emitting ability, and is usually mainly used as a stacked light-emitting device including an anode of applying positive voltage, a cathode of applying negative voltage, a hole injection/transport layer of injecting and transporting holes from the anode, an electron injection/transport layer of injecting and transporting electrons from the cathode, and a light-emitting layer of recombining the holes with the electrons to output light.

These metal complexes have significant light-emitting ability and are therefore extremely useful as host luminescent agents in the light-emitting device.

Furthermore, when a slight amount of these metal complexes is doped with a hole injection/transport layer material, an electron injection/transport layer material, or another host luminescent agent including a metal complex having 8-quinolinol as a ligand such as tris(8-hydroxyquinolinato) aluminum, these metal complexes function as guest luminescent agents to improve their emission efficiency and emission spectra.

Therefore, in a light-emitting device including one or a plurality of such materials as essential elements, these metal complexes may be extremely advantageously used alone or in combination with another luminescent agents such as dicyanomethylene (DCM), coumarin, perylene or rubrene or a hole injection/transport layer material and/or an electron injection/transport layer material, for example.

In a stacked light-emitting device, when luminescent agents also have hole injection/transport ability or electron injection/transport ability, a hole injection/transport layer or an electron injection/transport layer may be omitted, or when one of a hole injection/transport layer and an electron injection/transport layer functions as the other, the hole injection/transport layer or the electron injection/transport layer may be omitted, respectively.

The metal complexes of the present invention may be used for both a single-layer light-emitting device and a stacked light-emitting device.

An operation of a light-emitting device essentially includes a process of injecting electrons and holes from electrodes, a process of transferring the electrons and the holes in a solid, a process of recombining the electrons with the holes to produce a triplet exciton, and a process of allowing the exciton to emit light. These processes are essentially not different between a single-layer light-emitting device and a stacked light-emitting device.

However, a stacked light-emitting device may generally provide desired performance more easily as compared with a single-layer light-emitting device. While in the single-layer light-emitting device, characteristics of the four processes may be improved only by changing the molecular structure of a luminescent agent, in the stacked light-emitting device, functions required for each process may be shared by a plurality of materials and each material may be independently optimized. Thus, desired performance may be more easily achieved in a case where the metal complexes are formed in the stacked light-emitting device than in a case where the metal complexes are formed in the single-layer light-emitting device.

The aforementioned light-emitting device may be used in a display. Specifically, a display including the light-emitting device as a component may include the aforementioned metal complex in a light-emitting layer of the light-emitting device.

The present invention is not limited to the aforementioned best mode for carrying out the present invention. Obviously, various other embodiments can be provided without departing from the gist of the present invention.

EXAMPLES

Examples of the present invention will be specifically described. However, it should be noted that the present invention is not limited to these examples.

Example 1

A metal complex [PtCl(dppz)(dppzH)$_2$] was synthesized as a precursor complex, and [Pt$_2$Ag$_2$Cl$_2$(μ-dppz)$_4$(dppzH)$_2$], which is one of the first metal complex of the present invention, was synthesized by using this precursor complex.

Details of the synthetic method of the metal complex will be described below.

First, the intermediate product for synthesizing the precursor complex [PtCl(dppz)(dppzH)$_2$] was prepared.

Specifically, a solution of dppzH (136 mg, 0.62 mmol) in toluene (15 ml) was added to a suspension of [PtCl$_2$(C$_2$H$_5$CN)$_2$] (60 mg, 0.16 mmol) in toluene (5 ml), and the mixture was refluxed overnight under an Ar atmosphere. The resulting white yellow precipitate was collected, sequentially washed with toluene, hexane and diethyl ether, and then dried in vacuo. The yield was 137 mg. Chemical reaction to yield this white yellow solid is shown in chemical reaction formula 1.

[Chemical reaction formula 1]

This white yellow solid was identified by the IR spectrum.

The infrared frequencies are as follows.

IR (KBr): 3063 (br), 1572 (s), 1461 (s), 1271 (m), 1189 (m), 1107 (w), 1078 (m), 756 (s), 684 (s), 481 (w), 342 (w)

With regard to solubility in a solvent, the compound is slightly soluble in chloroform, dichloromethane, acetonitrile and methanol.

Next, the precursor complex [PtCl(dppz)(dppzH)$_2$] was synthesized from this white yellow solid.

Specifically, a solution of KOH (35 mg, 0.62 mmol) in methanol (2 ml) was added dropwise to a suspension of the white yellow solid (198 mg, 0.17 mmol) in methanol (18 ml) with stirring at room temperature, so that the solution immediately changed to a white suspension. After stirring for one hour, the formed white solid was collected, sequentially washed with methanol and water, and then dried in vacuo. The yield was (177 mg, 0.20 mmol). The synthetic method of [PtCl(dppz)(dppzH)$_2$] is shown in chemical reaction formula 2.

[Chemical reaction formula 2]

[PtCl(dppz)(dppzH)$_2$]

The metal complex was recrystallized from dichloromethane/methanol to yield a single crystal.

This complex exhibits weak pale orange luminescence in the solid state upon exposure to UV radiation.

With regard to solubility in a solvent, the compound is readily soluble in chloroform, dichloromethane and acetone and soluble in benzene, toluene and acetonitrile.

The product was identified by the IR and $^1$H NMR spectra.

The infrared frequencies are as follows.

IR (KBr): 3450 (w), 3111 (w), 3064 (w), 1603 (m), 1573 (m), 1464 (s), 1274 (w), 1212 (w), 1072 (m), 911 (w), 757 (s), 692 (s), 344 (w)

The $^1$H NMR data are summarized in Table 1.

TABLE 1

| $^1$H NMR of [PtCl(dppz)(dppzH)$_2$] (CDCl$_3$, TMS, 300 MHz) ||||
|---|---|---|---|
| δ (ppm) | Shape | Int. | Assign. |
| 8.12 | d | 4 | Ph of dppzH |
| 7.94 | d | 2 | Ph of dppz |
| 7.51–7.04 | m | 24 | Ph of dppz & dppzH |
| 6.45 | s | 2 | H4 of dppzH |
| 6.24 | s | 1 | H4 of dppz |

Next, the metal complex [Pt$_2$Ag$_2$Cl$_2$(μ-dppz)$_4$(dppzH)$_2$] was synthesized from the precursor complex [PtCl(dppz)(dppzH)$_2$].

Specifically, a solution of AgBF$_4$ (26 mg, 0.13 mmol) in acetonitrile (10 ml) was added to a solution of the precursor complex [PtCl(dppz)(dppzh)$_2$] (58 mg, 0.07 mmol) in acetonitrile (8 ml) at room temperature, and the mixture was stirred for two hours. Thereafter, the white solid was collected, washed with acetonitrile, and then dried in vacuo. The yield was 27 mg (0.014 mmol) (45%). The synthetic method of [Pt$_2$Ag$_2$Cl$_2$(μ-dppz)$_4$(dppzH)$_2$] is shown in chemical reaction formula 3.

[Chemical reaction formula 3]

This metal complex was recrystallized from chloroform/acetonitrile to yield a single crystal.

The metal complex [Pt$_2$Ag$_2$Cl$_2$(μ-dppz)$_4$(μ-dppzH)$_2$] exhibits strong orange luminescence in the solid state upon exposure to UV radiation.

With regard to solubility in a solvent, the compound is readily soluble in chloroform and dichloromethane.

The product was identified by the IR spectrum. The infrared frequencies are as follows.

IR (KBr): 3144 (w), 3060 (w), 1603 (w), 1570 (w), 1472 (s), 1460 (s), 1404 (m), 1334 (w), 1090 (m), 912 (w), 754 (s), 694 (s), 571 (w), 326 (w)

The results of elemental analysis of the product are shown in Table 2 by comparison with calculated values.

TABLE 2

Elemental Analysis of [Pt$_2$Ag$_2$Cl$_2$(μ-dppz)$_4$(dppzH)$_2$]

|  | calcd | found |
|---|---|---|
| C % | 54.20 | 53.84 |
| H % | 3.44 | 3.39 |
| N % | 8.43 | 8.46 |

Structures of the precursor complex and the finally produced metal complex will be described, respectively.

Molecular structures of [PtCl(dppz)(dppzH)$_2$] and [Pt$_2$Ag$_2$Cl$_2$(μ-dppz)$_4$(μ-dppzH)$_2$] were determined by single crystal X-ray structural analysis. The crystallographic data are shown in Table 3.

TABLE 3

Crystallographic data of [PtCl(dppz)(dppzH)$_2$]•CH$_3$OH and [Pt$_2$Ag$_2$Cl$_2$(μ-dppz)$_4$(μ-dppzH)$_2$]•2CH$_3$CN

|  | [PtCl(dppz)(dppzH)$_2$]•CH$_3$OH | [Pt$_2$Ag$_2$Cl$_2$(μ-dppz)$_4$(dppzH)$_2$]•2CH$_3$CN |
|---|---|---|
| empirical formula | C$_{46}$H$_{39}$ClN$_6$OPt | C$_{94}$H$_{74}$Ag$_2$Cl$_2$N$_{14}$Pt$_2$ |
| fw | 922.40 | 2076.53 |
| T, K | 296 | 296 |
| λ, Å | 0.71069 | 0.71070 |
| cryst syst | monoclinic | orthorhombic |
| space group | P2$_1$/n (14) | Pnna (#52) |
| a, Å | 15.905 (6) | 18.1830 (4) |
| b, Å | 9.712 (4) | 22.6303 (5) |
| c, Å | 27.34 (1) | 20.1687 (4) |
| α, deg | 90 | 90 |
| β, deg | 105.571 (2) | 90 |
| γ, deg | 90 | 90 |
| V, Å$^3$ | 4068.2 (2) | 8299.2 (5) |
| Z | 4 | 4 |
| ρ$_{calcd}$, Mg m$^{-3}$ | 1.506 | 1.662 |
| μ(Mo Kα), mm$^{-1}$ | 3.544 | 3.931 |
| no. of unique rflns | 9179 (R$_{int}$ = 0.029) | 9437(R$_{int}$ = 0.026) |
| data/restraints/params | 9175/0/508 | 9437/0/514 |
| final R indices [I > 2σ(I)] | R1 = 0.032 | R1 = 0.028 |
| R indices (all data) | R = 0.043, R$_w$ = 0.075 | R = 0.040, R$_w$ = 0.072 |
| GOF | 0.92 | 0.88 |

Here, the items in the table denote, from top to bottom, composition, formula weight, measured temperature, measured wavelength, crystal system, space group, lattice constants (a, b, c, α, β, γ), unit cell volume, Z value, density, linear absorption coefficient, number of unique reflections, numbers of data and parameters, final R index, R index when total reflection is used, and GOF value, respectively.

The metal complex [PtCl(dppz)(dppzH)$_2$] crystallized with a methanol molecule as a crystal solvent.

Figure 2:
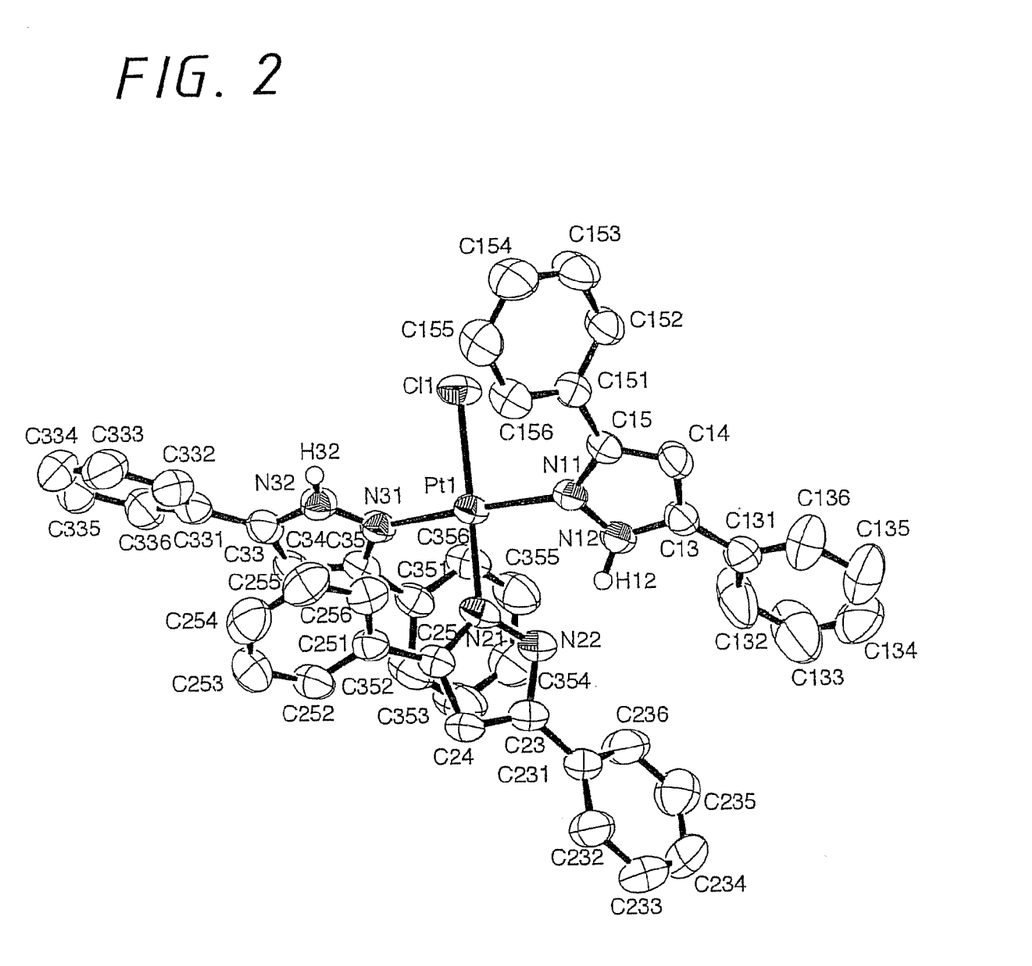
FIG. 2 is an ORTEP diagram showing a molecular structure of [PtCl(dppz)(dppzH)$_2$].

The molecular structure of the metal complex [PtCl(dppz)(dppzH)$_2$] is shown in the ORTEP diagram of FIG. 2.

As shown in FIG. 2, the metal complex [PtCl(dppz)(dppzH)$_2$] has a structure in which one Cl$^-$ ion, one dppz ligand and two dppzH ligands coordinate to the Pt$^{II}$ ion. One of the two dppzH ligands forms a hydrogen bonding (N12-H12 . . . N22) together with the dppz ligand.

Figure 3:
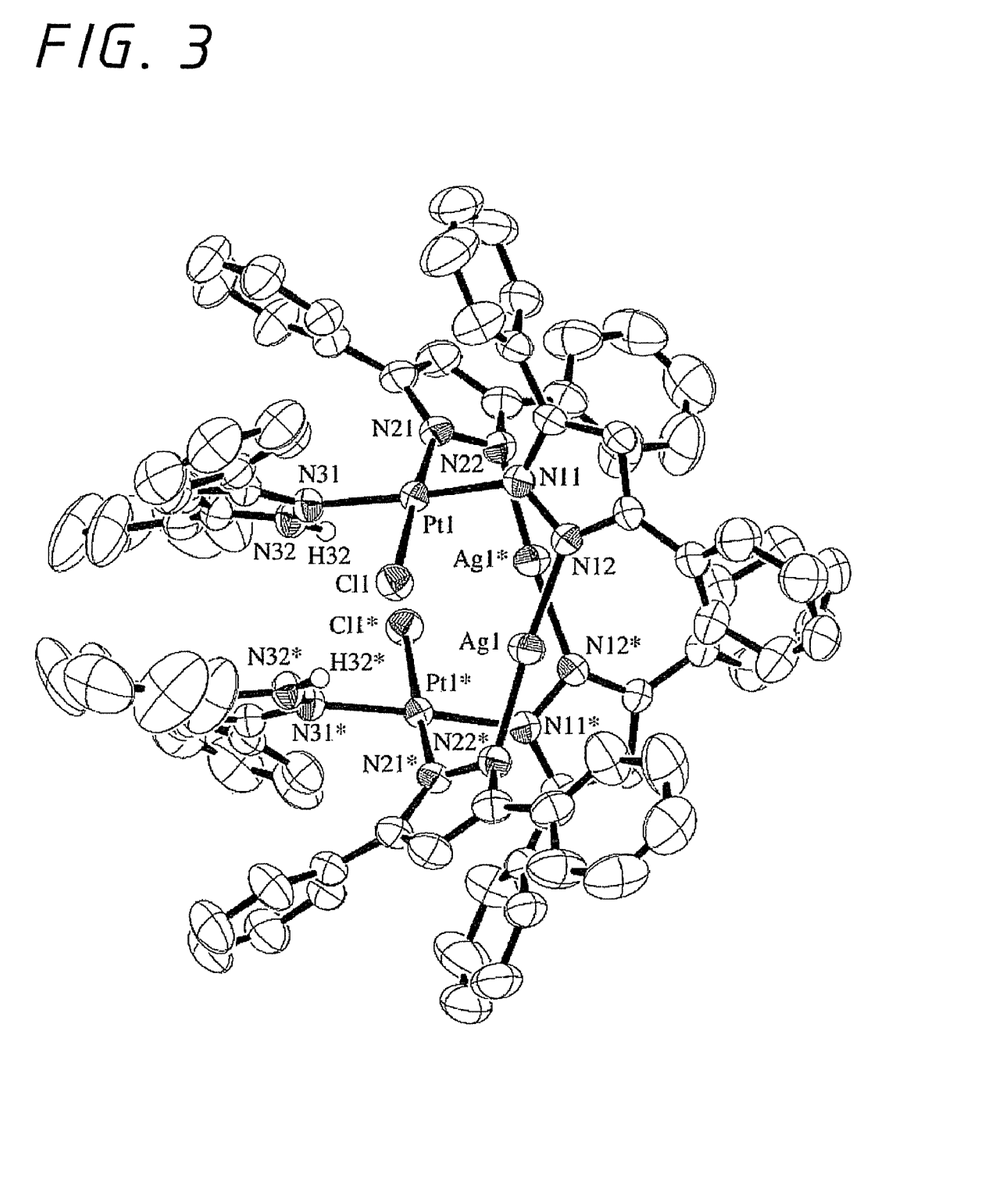
FIG. 3 is an ORTEP diagram showing a molecular structure of [Pt$_2$Ag$_2$Cl$_2$(μ-dppz)$_4$(dppzH)$_2$].

The molecular structure of [Pt$_2$Ag$_2$Cl$_2$(μ-dppz)$_4$(dppzH)$_2$] is shown in the ORTEP diagram of FIG. 3.

As shown in FIG. 3, two protons (H$^+$) in total are liberated from two molecules of [PtCl(dppz)(dppzH)$_2$] and two Ag$^I$ ions are incorporated in the molecules to form one molecule of [Pt$_2$Ag$_2$Cl$_2$(μ-dppz)$_4$(dppzH)$_2$]. One Cl$^-$ ion, two dppz ligands and one dppzH ligand coordinate to each Pt$^{II}$ ion, and each Ag$^I$ ion is located between the two dppz ligands. The molecule has a crystallographically imposed 2-fold axis passing through the midpoint of Pt1 . . . Pt1* and the midpoint of Ag1 . . . Ag1*, and half of the atoms in the molecule are independent.

The Pt . . . Pt distance in [Pt$_2$Ag$_2$Cl$_2$(μ-dppz)$_4$(dppzH)$_2$] is 4.2844 (3) Å. The Pt . . . Ag distances are 3.2153 (3) and 3.4552 (3) Å, and the Ag . . . Ag distance is 3.1109 (7) Å.

[Pt$_2$Ag$_2$Cl$_2$(μ-dppz)$_4$(dppzH)$_2$] exhibits bright orange luminescence in the solid state upon exposure to UV radiation at 300 nm or 350 nm, and its emission spectrum has the local maximum at 629 nm. The emission lifetime is 5.78 μs. On the other hand, the complex exhibits a broad emission spectrum at 521 nm in dichloromethane, but the emission intensity is drastically decreased from that in the solid state.

It should be noted that the metal complex [Pt$_2$Ag$_2$Cl$_2$(μ-dppz)$_4$(dppzH)$_2$] exhibits orange luminescence considerably brighter than that of the metal complex [Pt$_2$Ag$_4$(μ-Cl)$_2$(μ-dppz)$_6$] in the solid state.

The addition of AgBF$_4$ and Et$_3$N to the metal complex [Pt$_2$Ag$_2$Cl$_2$(μ-dppz)$_4$(dppzH)$_2$] yielded [Pt$_2$Ag$_4$(μ-Cl)$_2$(μ-dppz)$_6$] as described above. The synthetic method of the metal complex [Pt$_2$Ag$_4$(μ-Cl)$_2$(μ-dppz)$_6$] is shown in chemical reaction formula 4.

[Chemical reaction formula 4]

[Pt$_2$Ag$_4$(μ-Cl)$_2$(μ-dppz)$_6$]

The metal complex [Pt$_2$Ag$_4$(μ-Cl)$_2$(μ-dppz)$_6$] exhibits bright orange luminescence in the solid state and weak green luminescence in solution, respectively, upon exposure to UV radiation.

With regard to solubility in a solvent, the compound is readily soluble in chloroform and dichloromethane, soluble in benzene and toluene, and slightly soluble in acetonitrile.

The product was identified by the IR spectrum. The infrared frequencies are as follows.

IR (KBr): 3061 (w), 1603 (m), 1472 (s), 1403 (m), 1334 (w), 1279 (w), 1111 (w), 1072 (w), 912 (w), 754 (s), 696 (s), 304(w)

The results of elemental analysis of the product are shown in Table 4 by comparison with calculated values.

TABLE 4

Elemental Analysis of [Pt$_2$Ag$_4$Cl$_2$(dppz)$_6$]

|       | Calc. | Found | Δ     |
|-------|-------|-------|-------|
| C (%) | 48.95 | 48.84 | −0.11 |
| H (%) | 3.01  | 2.90  | −0.11 |
| N (%) | 7.61  | 7.64  | 0.03  |

The molecular structure of the metal complex [Pt$_2$Ag$_4$(μ-Cl)$_2$(μ-dppz)$_6$] was also determined by single crystal X-ray structural analysis. The crystallographic data are shown in Table 5.

TABLE 5

Crystallographic data of [Pt$_2$Ag$_4$(μ-Cl)$_2$(μ-dppz)$_6$]

|  | [Pt$_2$Ag$_4$(μ-Cl)$_2$(μ-dppz)$_6$] |
|---|---|
| empirical formula | C$_{90}$H$_{66}$Cl$_2$N$_{16}$Ag$_4$Pt$_2$ |
| fw | 2264.18 |
| T, K | 296 |
| λ, Å | 0.71069 |
| cryst syst | monoclinic |
| space group | P2$_1$/n (14) |
| a, Å | 15.229 (4) |
| b, Å | 29.469 (7) |
| c, Å | 19.231 (4) |
| α, deg | 90 |
| β, deg | 92.2363 (8) |
| γ, deg | 90 |

TABLE 5-continued

| Crystallographic data of [Pt$_2$Ag$_4$(μ-Cl)$_2$(μ-dppz)$_6$] | |
|---|---|
| | [Pt$_2$Ag$_4$(μ-Cl)$_2$(μ-dppz)$_6$] |
| V, Å$^3$ | 8624.0 (2) |
| Z | 4 |
| $\rho_{calcd}$, Mg m$^{-3}$ | 1.744 |
| μ (Mo Kα), mm$^{-1}$ | 4.223 |
| no. of unique rflns | 18976 (R$_{int}$ = 0.030) |
| data/restraints/params | 18976/0/991 |
| final R indices [I > 2σ(I)] | R1 = 0.050 |
| R indices (all data) | R = 0.081, R$_w$ = 0.161 |
| GOF | 1.33 |

Figure 4:
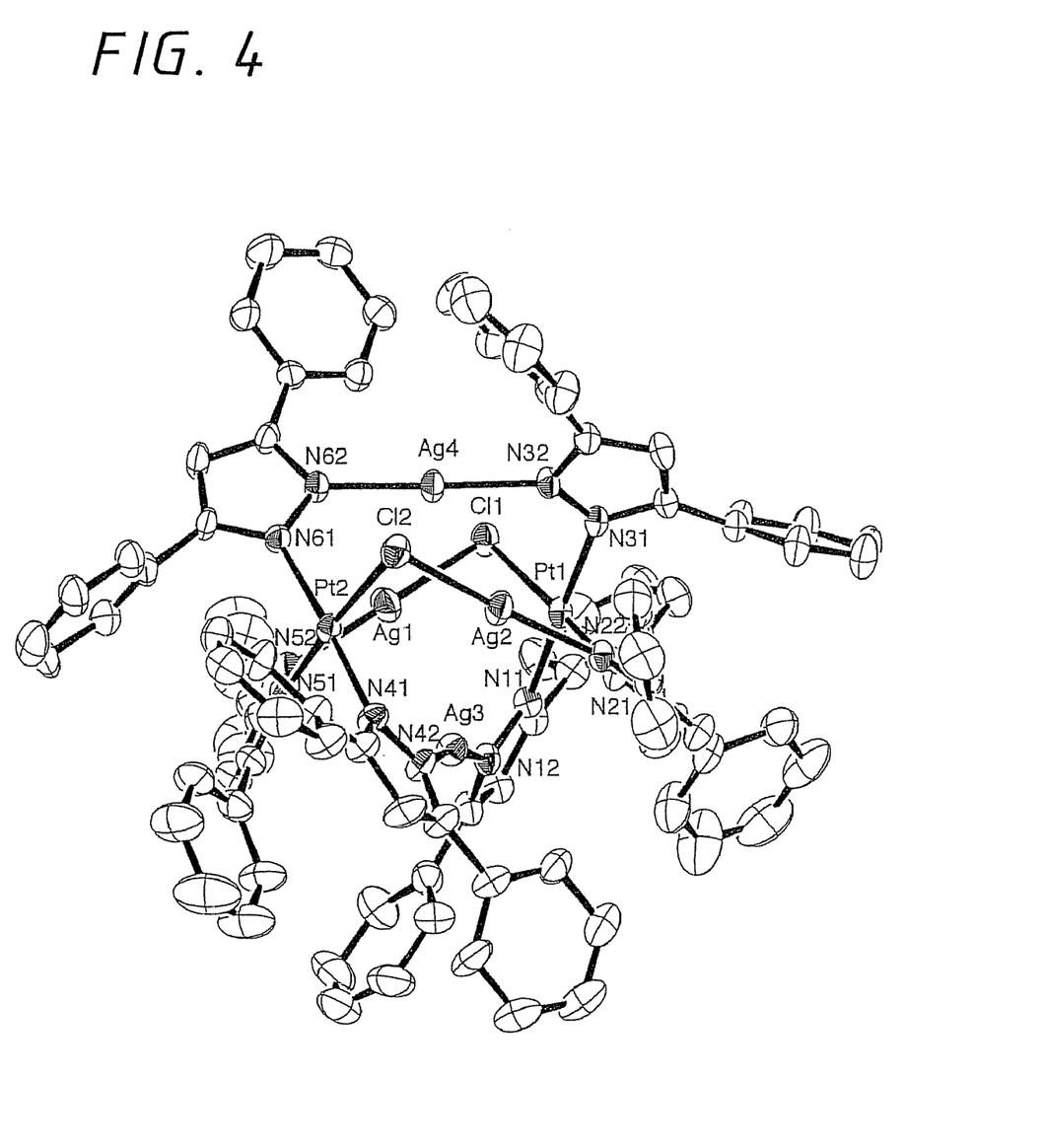
FIG. 4 is an ORTEP diagram showing a molecular structure of [Pt$_2$Ag$_4$(μ-Cl)$_2$(μ-dppz)$_6$].

The molecular structure of [Pt$_2$Ag$_4$(μ-Cl)$_2$(μ-dppz)$_6$] is shown in the ORTEP diagram of FIG. 4.

As shown in FIG. 4, four protons (H$^+$) in total are liberated from two molecules of [PtCl(dppz)(dppzH)$_2$] and four Ag$^I$ ions are incorporated in the molecules to form one molecule of the metal complex [Pt$_2$Ag$_4$(μ-Cl)$_2$(μ-dppz)$_6$]. One Cl$^-$ ion and three dppz ligands coordinate to each Pt$^{II}$ ion, and each Ag$^I$ ion is located between the two dppz ligands or between the Cl$^-$ ion and the dppz ligand. The complex molecule has an idealized 2-fold axis passing through Ag3 atom and Ag4 atom and the complex also has an idealized mirror plane defined by Pt1, Pt2, Ag3 and Ag4.

The Pt . . . Pt distance in [Pt$_2$Ag$_4$(μ-Cl)$_2$(μ-dppz)$_6$] is 5.2873 (5) Å. The Pt . . . Ag distances are ranging from 3.0816 (8) to 3.6535 (7) Å, and the proximate Ag . . . Ag distances are ranging from 2.936 (1) to 4.725 (1) Å.

[Pt$_2$Ag$_4$(μ-Cl)$_2$(μ-dppz)$_6$] exhibits bright orange luminescence in the solid state upon exposure to UV radiation at 300 nm or 350 nm, and its emission spectrum has the local maximum at 652 nm. The complex exhibits a broad emission spectrum around 450 nm to 600 nm in dichloromethane, but the shape of the spectrum is changed gradually with increasing the emission intensity.

Example 2

[Pt$_2$Cu$_2$Cl$_2$(μ-dppz)$_4$(dppzH)$_2$], which is one of the first metal complex of the present invention, was synthesized by using the precursor complex [PtCl(dppz)(dppzH)$_2$] also used in Example 1.

First, the precursor complex [PtCl(dppz)(dppzH)$_2$] was synthesized as in Example 1.

Next, the metal complex [Pt$_2$Cu$_2$Cl$_2$(μ-dppz)$_4$(dppzH)$_2$] was synthesized from the precursor complex [PtCl(dppz)(dppzH)$_2$].

Specifically, a solution of [Cu(CH$_3$CN)$_4$]BF$_4$ (61 mg, 0.18 mmol) in dichloromethane (13 ml) was added to a solution of the precursor complex [PtCl(dppz)(dppzH)$_2$] (149 mg, 0.17 mmol) in dichloromethane (7 ml) at room temperature under an argon atmosphere. Et$_3$N (18 mg, 0.18 mmol) was further added to the solution, and the mixture was stirred for six hours. Since no precipitate was observed, the solution was concentrated to dryness by an evaporator, and the solid was washed with acetonitrile. Thereafter, the white solid was collected, washed with a small amount of diethyl ether, and then dried in vacuo. The yield was 128 mg (0.13 mmol) (74%). The synthetic method of [Pt$_2$Cu$_2$Cl$_2$(μ-dppz)$_4$(dppzH)$_2$] is shown in chemical reaction formula 5.

[Chemical reaction formula 5]

With regard to solubility in a solvent, the compound is readily soluble in chloroform and dichloromethane.

The product was identified by the IR spectrum. The infrared frequencies are as follows.

IR (KBr): 3142 (m), 3061 (m), 1604 (w), 1571 (w), 1473 (s), 1406 (w), 1337 (w), 1099 (w), 911 (w), 754 (s), 695 (s), 574 (w), 316 (w)

The results of elemental analysis of the product are shown in Table 6 by comparison with calculated values.

TABLE 6

| Elemental Analysis of [Pt$_2$Cu$_2$Cl$_2$(μ-dppz)$_4$(dppzH)$_2$] | | |
|---|---|---|
| | calcd | found |
| C % | 56.72 | 56.43 |
| H % | 3.60 | 3.41 |
| N % | 8.82 | 8.86 |

The structure of the finally produced metal complex will be described.

The molecular structure of [Pt$_2$Cu$_2$Cl$_2$(μ-dppz)$_4$(dppzH)$_2$] was determined by single crystal X-ray structural analysis. The crystallographic data are shown in Table 7.

TABLE 7

Crystallographic data of [Pt$_2$Cu$_2$Cl$_2$(μ-dppz)$_4$(dppzH)$_2$]·2CH$_3$CN

| | [Pt$_2$Cu$_2$Cl$_2$(μ-dppz)$_4$(dppzH)$_2$]·2CH$_3$CN |
|---|---|
| empirical formula | C$_{94}$H$_{74}$Cu$_2$Cl$_2$N$_{14}$Pt$_2$ |
| fw | 1987.89 |
| T, K | 296 |
| λ, Å | 0.71070 |
| cryst syst | orthorhombic |
| space group | Pnna (#52) |
| a, Å | 18.3146 (5) |
| b, Å | 22.6251 (5) |
| c, Å | 19.7815 (5) |
| α, deg | 90 |
| β, deg | 90 |
| γ, deg | 90 |
| V, Å$^3$ | 8196.9 (4) |
| Z | 4 |
| ρcalcd, Mg m$^{-3}$ | 1.611 |
| μ (Mo Kα), cm$^{-1}$ | 40.23 |
| no. of unique rflns | 9383 (R$_{int}$ = 0.027) |
| data/restraints/params | 9141/0/514 |
| final Rindices [I > 2σ(I)] | R1 = 0.028 |
| Rindices (all data) | R = 0.042, R$_W$ = 0.065 |
| GOF | 0.99 |

[Pt$_2$Cu$_2$Cl$_2$(μ-dppz)$_4$(dppzH)$_2$] is crystallized with two acetonitrile molecules, and its crystal structure is isomorphous to that of [Pt$_2$Ag$_2$Cl$_2$(μ-dppz)$_4$(dppzH)$_2$]·2CH$_3$CN.

Figure 5:
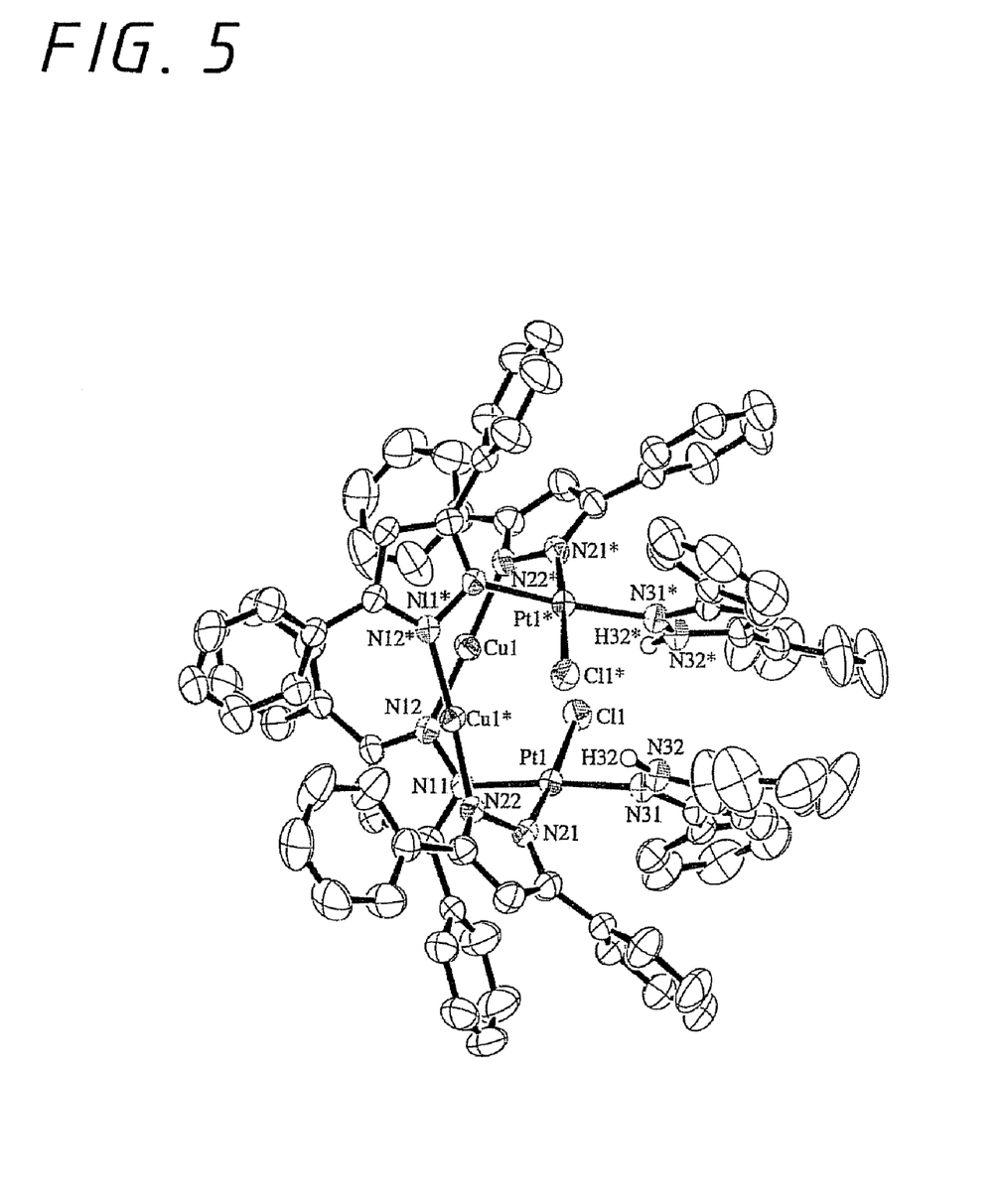
FIG. 5 is an ORTEP diagram showing a molecular structure of [Pt$_2$Cu$_2$Cl$_2$(μ-dppz)$_4$(dppzH)$_2$].

The molecular structure of [Pt$_2$Cu$_2$Cl$_2$(μ-dppz)$_4$(dppzH)$_2$] is shown in the ORTEP diagram of FIG. 5.

As shown in FIG. 5, two protons (H$^+$) in total are liberated from two molecules of [PtCl(dppz)(dppzH)$_2$] and two Cu$^I$ ions are incorporated in the molecules to form one molecule of [Pt$_2$Cu$_2$Cl$_2$(μ-dppz)$_4$(dppzH)$_2$], which is similar to the molecular structure of [Pt$_2$Ag$_2$Cl$_2$(μ-dppz)$_4$(dppzh)$_2$]. One Cl$^-$ ion, two dppz ligands and one dppzH ligand coordinate to each Pt$^{II}$ ion, and each Cu$^I$ ion is located between the two dppz ligands. The molecule has a crystallographically imposed 2-fold axis passing through the midpoint of Pt1 . . . Pt1* and the midpoint of Cu1 . . . Cu1*, and half of the atoms in the molecule are independent.

The Pt . . . Pt distance in [Pt$_2$Cu$_2$Cl$_2$(μ-dppz)$_4$(dppzH)$_2$] is 3.9612 (3) Å. The Pt . . . Cu distances are 3.2126 (5) and 3.3454 (5) Å, and the Cu . . . Cu distance is 3.145 (1) Å.

Example 3

[Pt$_2$Ag$_2$Cu$_2$(μ-Cl)$_2$(μ-dppz)$_6$], which is one of the second metal complex of the present invention, was synthesized by using the first metal complex [Pt$_2$Ag$_2$Cl$_2$(μ-dppz)$_4$(μ-dppzH)$_2$] of the present invention prepared in Example 1 as a precursor.

Details of the synthetic method of the metal complex will be described below.

The metal complex [Pt$_2$Ag$_2$Cu$_2$(μ-Cl)$_2$(μ-dppz)$_6$] was synthesized from the metal complex [Pt$_2$Ag$_2$Cl$_2$(μ-dppz)$_4$(dppzH)$_2$].

Specifically, Et$_3$N (6 mg, 0.06 mmol) was added to a solution of [Pt$_2$Ag$_2$Cl$_2$(μ-dppz)$_4$(dppzH)$_2$] (62 mg, 0.03 mmol) in dichloromethane (8 ml) at room temperature under an argon atmosphere. The mixture became yellow immediately by further adding a solution of [Cu(CH$_3$CN)$_4$]BF$_4$ (18 mg, 0.06 mmol) in dichloromethane (8 ml). The suspension was changed to a yellow transparent solution by stirring for about 45 minutes. The solution became paler thereafter. Stirring was performed for six hours in total. Since no precipitate was observed after completion of the reaction, the solution was concentrated to dryness by an evaporator, and the solid was washed with acetonitrile. The white yellow solid was collected and dried in vacuo. The yield was 51 mg (0.02 mmol) (80%).

The synthetic method of the metal complex [Pt$_2$Ag$_2$Cu$_2$(μ-Cl)$_2$(μ-dppz)$_6$] is shown in chemical reaction formula 6.

[Chemical reaction formula 6]

This compound exhibits orange luminescence upon exposure to UV radiation.

With regard to solubility in a solvent, the compound is readily soluble in chloroform and dichloromethane.

The product was identified by the IR spectrum and elemental analysis.

The infrared frequencies are as follows.

IR (KBr): 3061 (m), 1604 (w), 1541 (w), 1473 (s), 1405 (m), 1337 (w), 1157 (w), 1113 (m), 1072 (w), 1005 (w), 913 (w), 754 (s), 695 (s), 569 (w), 521 (w), 315 (w)

The results of elemental analysis of the product are shown in Table 8 by comparison with calculated values.

TABLE 8

Elemental Analysis of [Pt$_2$Ag$_2$Cu$_2$(μ-Cl)$_2$(μ-dppz)$_6$]

| | calcd | found |
|---|---|---|
| C % | 51.00 | 50.63 |
| H % | 3.14 | 2.96 |
| N % | 7.93 | 7.87 |

Further, mass spectroscopy was performed by FABMS. The result is as follows.

FABMS: m/z=2119.1 [M⁺]

As described above, the metal complexes of the present invention have potential for industrial applications such as light-emitting device and display.

DESCRIPTION OF SYMBOLS

1 Substrate
2 Anode
3 Hole injection layer
4 Hole transport layer
5 Light-emitting layer
6 Electron transport layer
7 Electron injection layer
8 Cathode

The invention claimed is:

1. A metal complex comprising the following composition:

$$[(Pt^{II})_2(M^I)_2(X)_2(L)_4(LH)_2]$$

wherein $M^I$ denotes $Ag^I$, $Au^I$ or $Cu^I$, X is Cl, Br or I, L denotes a structure represented by the formula (1):

(1)

and LH denotes a structure represented by the formula (2):

(2)

wherein $R^1$, $R^2$ and $R^3$ independently denote a hydrogen atom, a chlorine atom, a bromine atom, an iodine atom, a hydroxyl group, a phenyl group, a trifluoromethylphenyl group, a pentafluorophenyl group, a naphthyl group, a methyl group, an ethyl group, an i-propyl group, a t-butyl group, a trifluoromethyl group, a hydroxymethyl group or a hydroxyethyl group.

2. The metal complex according to claim 1, wherein at least one of $R^1$, $R^2$ and $R^3$ in the formulas is not a hydrogen atom.

3. A light-emitting device wherein the light-emitting device comprises a light-emitting layer including the metal complex according to claim 1.

4. A display wherein the display comprises the light-emitting device according to claim 3.

5. A metal complex comprising the following composition:

$$[(Pt^{II})_2(Ag^I)_2(Cu^I)_2(X)_2(L)_6]$$

wherein X is Cl, Br or I, and L denotes a structure represented by the formula (1):

(1)

wherein $R^1$, $R^2$ and $R^3$ independently denote a hydrogen atom, a chlorine atom, a bromine atom, an iodine atom, a hydroxyl group, a phenyl group, a trifluoromethylphenyl group, a pentafluorophenyl group, a naphthyl group, a methyl group, an ethyl group, an i-propyl group, a t-butyl group, a trifluoromethyl group, a hydroxymethyl group or a hydroxyethyl group.

6. The metal complex according to claim 5, wherein at least one of $R^1$, $R^2$ and $R^3$ in the formulas is not a hydrogen atom.

7. A light-emitting device wherein the light-emitting device comprises a light-emitting layer including the metal complex according to claim 5.

8. A display wherein the display comprises the light-emitting device according to claim 7.

9. A light-emitting device wherein the light-emitting device comprises a light-emitting layer including the metal complex according to claim 2.

10. A light-emitting device wherein the light-emitting device comprises a light-emitting layer including the metal complex according to claim 6.

* * * * *